(12) United States Patent
Bockelmann et al.

(10) Patent No.: US 7,993,825 B2
(45) Date of Patent: Aug. 9, 2011

(54) DETECTION OF MOLECULAR PROBES FIXED TO AN ACTIVE ZONE OF A SENSOR

(75) Inventors: Ulrich Bockelmann, Paris (FR); Francois Pouthas, Heidelberg (DE)

(73) Assignee: Centre National de la Recherche Scientifique, Paris (FR)

( * ) Notice: Subject to any disclaimer, the term of this patent is extended or adjusted under 35 U.S.C. 154(b) by 568 days.

(21) Appl. No.: 10/501,772

(22) PCT Filed: Dec. 11, 2002

(86) PCT No.: PCT/FR02/04283
§ 371 (c)(1), (2), (4) Date: Apr. 25, 2005

(87) PCT Pub. No.: WO03/062811
PCT Pub. Date: Jul. 31, 2003

(65) Prior Publication Data
US 2006/0011911 A1    Jan. 19, 2006

(30) Foreign Application Priority Data
Jan. 21, 2002 (FR) .................................. 02 00676

(51) Int. Cl.
*C12Q 1/68* (2006.01)
*C12M 1/34* (2006.01)
*C12M 3/00* (2006.01)
*G01N 33/48* (2006.01)
*G01N 33/50* (2006.01)

(52) U.S. Cl. ............................ 435/6; 435/287.2; 702/19
(58) Field of Classification Search ........... 435/6, 287.2; 702/19
See application file for complete search history.

(56) References Cited

U.S. PATENT DOCUMENTS

| | | | | |
|---|---|---|---|---|
| 5,164,319 A * | 11/1992 | Hafeman et al. | ............ | 435/287.1 |
| 5,242,793 A * | 9/1993 | Kariyone et al. | ......... | 204/403.11 |
| 5,466,348 A * | 11/1995 | Holm-Kennedy | ............ | 205/775 |
| 5,496,699 A * | 3/1996 | Sorenson | ........................... | 435/6 |
| 5,498,521 A * | 3/1996 | Dryja et al. | ........................ | 435/6 |
| 5,653,939 A * | 8/1997 | Hollis et al. | ....................... | 506/3 |
| 5,805,014 A * | 9/1998 | Price | ............................ | 327/427 |
| 5,922,591 A * | 7/1999 | Anderson et al. | ........... | 435/287.2 |
| 6,203,981 B1 * | 3/2001 | Ackley et al. | ...................... | 435/6 |
| 6,281,006 B1 * | 8/2001 | Heller et al. | ................ | 435/287.9 |
| 6,322,963 B1 | 11/2001 | Bauer | | |
| 6,331,274 B1 | 12/2001 | Ackley et al. | | |
| 7,908,088 B2 * | 3/2011 | Bockelmann et al. | ........... | 702/19 |
| 2001/0024788 A1 * | 9/2001 | Hashimoto | ........................ | 435/6 |
| 2003/0190608 A1 * | 10/2003 | Blackburn | ......................... | 435/6 |
| 2004/0238379 A1 * | 12/2004 | Lindsay et al. | ................ | 205/792 |

* cited by examiner

Primary Examiner — Robert T. Crow
(74) Attorney, Agent, or Firm — Oblon, Spivak, McClelland, Maier & Neustadt, L.L.P.

(57) ABSTRACT

The present invention relates to a method for detecting at least one parameter representative of molecular probes fixed to zones of a sensor.

18 Claims, 12 Drawing Sheets

DETECTION OF MOLECULAR PROBES FIXED TO AN ACTIVE ZONE OF A SENSOR

The present invention relates to a method for detecting at least one parameter representative of molecular probes fixed to zones of a sensor.

A method for detecting the hydridization of DNA sequences using a field-effect transistor is already known, as was described in the article by E. SOUTEYRAND et al., entitled "Direct Detection of the hybridization of synthetic Homo-Oligomer DNA Sequences by Field Effect", published in 1997 in J. Phys. Chem. B1997, 101, pages 2980 to 2985. A transistor of the ISFET ("Ion-Sensitive Field-Effect Transistor") type which can be used in this type of application has been described in the article by Piet BERGVELD "Development, Operation and Application of the ISFET as a Tool for Electrophysiology", published in IEEE Transactions on Biomedical Engineering Volume BME-19—No. 5 Sep. 1972 pages 342 to 351. Indications on the fabrication of such transistor structures can be found in the article by V. KIESSLING et al., entitled "Extracellular Resistance in Cell Adhesion Measured with a Transistor Probe", published in Langmuir 2000, 16, pages 3517-3521. Finally, a surface preparation method has been described in the article by A. KUMAR et al., entitled "Silanized nucleid acids: a general platform for DNA immobilization", published in Nucleic Acid Research 2000, Volume 28, No. 14, pages i to vi.

Two methods for fixing the molecular probes to the surface can in particular be used in the context of the present invention. The first consists of direct synthesis on a solid phase, as described, for example, in the article by S. P. A. Fodor et al., entitled "Light-directed, spatially addressable parallel chemical synthesis", published in Science 251, pages 767 to 773 (1991). The second is the fixing of the molecules using a dilution.

In the case of sensors comprising a plurality of active zones, for example DNA chips or protein chips, no available technique currently exists for readily controlling, in a relatively rapid manner, the zones on which molecular probes have effectively been fixed.

An aim of the present invention is thus a method for detecting at least one parameter representative of molecular probes fixed to at least one zone of a sensor, in particular for the purpose of controlling the local deposition and the local fixing of the molecular probes, so as to make it possible in particular to remedy at least partially the problems posed by the considerable experimental variations which are frequently encountered in practice.

The present invention thus relates to a method for detecting at least one parameter representative of molecular probes fixed to at least one active zone of a sensor, characterized in that said sensor consists of a network of field-effect transistors, each of which has a source region, a drain region, and a gate region which forms a said active zone on which said parameter representative of the molecular probes should be detected, and in that it comprises the following steps:
 a) bringing some of said zones into contact with molecular probes in order to fix said probes,
 b) bathing at least these zones which have been brought into contact with molecular probes, in an electrolyte solution,
 c) measuring at least one point of the drain current/source-gate voltage/source-drain voltage characteristic of at least two of the transistors of the first group corresponding to zones brought into contact with molecular probes, for example by applying to these transistors of the first group, the drain and the source of which have been biased, a given voltage, for example a constant voltage, between the gate and the source, or alternatively a given drain current, for example a constant current, so as to deduce therefrom at least one said representative parameter by comparison between at least two of the measurements obtained for two different zones. Said comparison is preferably carried out using a differential measurement. The representative parameter may be detection of the fixing of molecular probes.

Between steps a and b, rinsing may be envisioned.

According to a particular embodiment, the method is characterized in that it comprises, after a) and before b), the following steps:
 a1) rinsing,
 a2) adding a solution containing target molecules capable of interacting specifically with the molecular probes, for example of hybridizing with them, when the molecular probes are DNA, optionally followed by rinsing.

According to another particular embodiment, the method is characterized in that it comprises, after c, the following steps:
 d) adding an electrolyte solution containing target molecules capable of interacting specifically with the molecular probes, for example of hybridizing when the molecular probes are DNA,
 e) measuring at least one point of the drain current/source-gate voltage/source-drain voltage characteristic of at least two of the transistors of a second group corresponding to zones brought into contact with molecular probes and with target molecules, for example by applying a voltage, for example a constant voltage, between the gate and the source of these transistors of the second group, the drain and the source of which have been biased, or a given current, for example a constant current, to the source of these transistors of the second group, so as to obtain by comparison at least one said representative parameter.

The method can use a plurality of said measurements of at least one point of the characteristic, which are spaced out in time. This makes it possible to obtain a measurement which is doubly comparative, in space and over time.

According to a first variant, the comparison, in particular by differential measurement, is carried out between at least two transistors corresponding to zones which are bathed in an electrolyte solution, after having been brought into contact with molecular probes.

According to a preferred second variant, this comparison, in particular by differential measurement, is carried out between at least one transistor corresponding to a zone which is bathed in a said electrolyte solution, after having been brought into contact with molecular probes, and at least one transistor corresponding to a zone which is bathed in said electrolyte solution without having been brought into contact, beforehand, with molecular probes.

The molecular probes are, for example, DNA, RNA or protein molecules.

The method according to the invention is compatible with a conventional detection of molecular interaction by fluorescence.

Other characteristics and advantages of the invention will emerge more clearly on reading the description hereinafter, in connection with the attached drawings in which.

Figure 1:
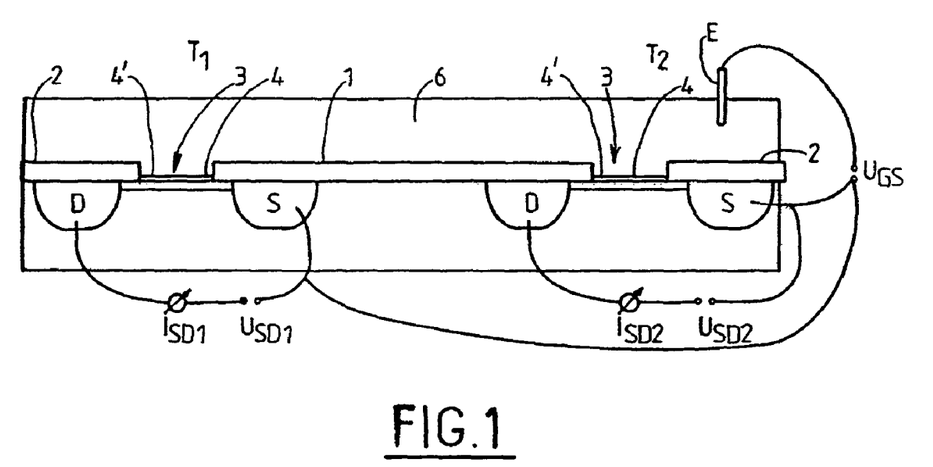
FIG. 1 represents two field-effect transistors of a detection chip comprising a plurality of such transistors organized according to a one-dimensional or two-dimensional network of transistors.
Figure 2:
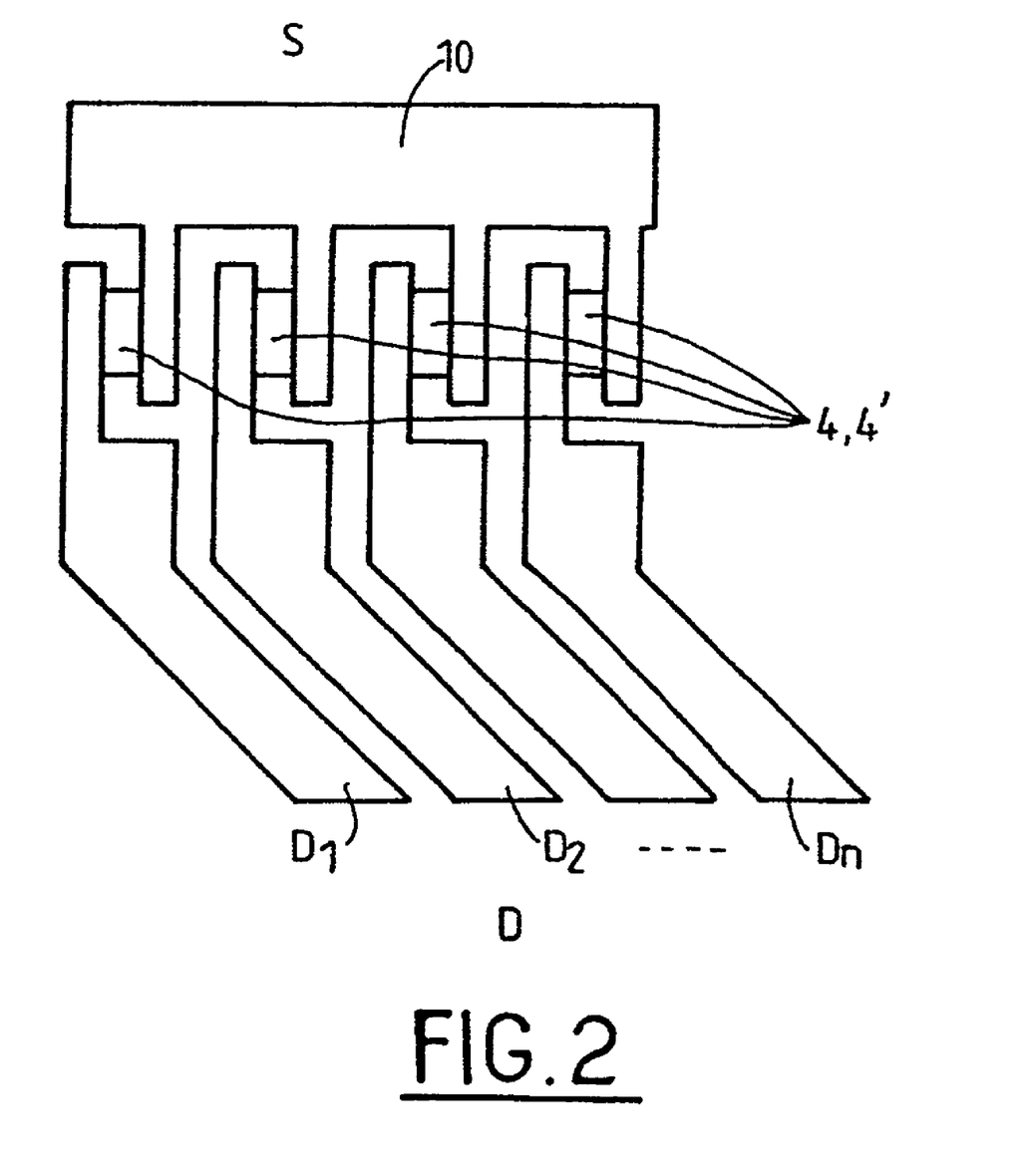
FIG. 2 represents, viewed from above, details of a detection chip and the arrangement of the active zones each corresponding to a field-effect transistor.
Figure 3:
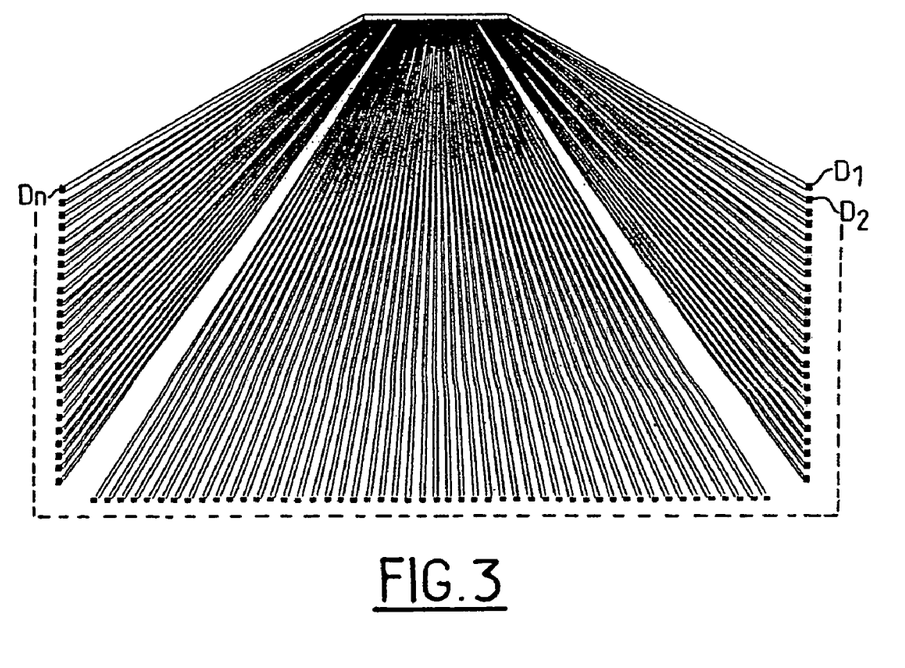
FIG. 3 illustrates the electrical drain connections of the transmissions of the one-dimensional or two-dimensional network, FIG. 4 representing the resistance of the various electrical drain connections, curve A representing the calculated values and curve B the measured values, the difference between the curves being due mostly to the channel resistance which is constant.

FIGS. 1 to 3 illustrate a sensor having a network of field-effect transistors on a silicon substrate. A transistor $T_1$ or $T_2$ represented as a sectional view in FIG. 1 is provided with a source region S and a drain region D which each present an electrical contact and which are surmounted by an insulating layer respectively 1 and 2, for example an $SiO_2$ thermal oxide. The active region 3 between the source S and the drain D forms the gate region G of the transistor and has a thin insulating layer 4, for example a layer of thermal $SiO_2$. It is also possible not to have oxide on this active region. The active surface is then delimited by a portion 4' of the substrate which is stripped of insulating material.

Molecular probes, for example single stranded DNA molecules, are fixed by a known method to at least some of the active surfaces 4 or 4'. For DNA, use is preferably made of depleted n-channel field-effect transistors (for which the charge carriers are electrons, which are more mobile, hence an increase in sensitivity) with a negative gate bias (i.e. the electrolyte is negatively biased with respect to the semiconductor), the DNA being negatively charged (for an electrolyte of neutral pH).

The application of a source-drain voltage $U_{SD}$ between the source S and the drain D ($U_{SD1}$ for $T_1$, and $U_{SD2}$ for $T_2$) and of a gate-source voltage $U_{GS}$ between the electrolyte 6 and the source S (for example by means of a single Ag/AgCl electrode E) induces a two-dimensional gas of charge carriers at the Si/SiO$_2$ interface, or at the Si/electrolyte interface of each resistor. A drain current $I_D$ results therefrom which, for each transistor, depends substantially on the charge at the SiO$_2$/electrolyte or Si/electrolyte interface. This interface which faces the channel between the source S and the drain D is referred to as active surface.

The current $I_D$ depends on the fixing of the molecular probes, for example of the DNA molecules, to the active surface 4 or 4'.

As shown in FIGS. 2 and 3, n structures of field-effect transistor type are integrated into a silicon substrate covered with an insulator (SiO$_2$ or other) and provided with appropriate connections (metallization or preferably doped conductive regions) by means of the electrical connections of the source 10 and of the drain ($D_1, \ldots D_n$. Unlike a standard MOS transistor structure there is no metal gate electrode. This corresponds to the structure of "ISFET" (Ion Sensitive Field Effect Transistor) type. A substrate of SOI (silicon-on-isolator) type, which provides a higher sensitivity, is preferably used.

The various structures are laterally close to one another and their active surfaces are in contact with the same measuring solution. A typical lateral dimension in current microelectronics is less than a µm. In the DNA chip technology as used in the present invention, the lateral dimension is 5-10 µm for direct synthesis on the solid phase and 50-100 µm in the case of fixing of the molecules using a dilution.

In the present parallel measurement configuration, several plots with various types of immobilized molecular probes are in contact with the same measuring solution and at least one transistor structure is located below each plot. The use of several transistors per plot is possible in view of the above-mentioned dimensions and permits redundancy in the detection.

An electrode E (Ag/AgCl, for example) is used to set the potential of the measuring solution 6 (electrolyte) with respect to the silicon structure that it covers and to set the operating point of the sensors (transistors). The potential of the electrolyte 6 can, in certain cases, be equal to zero. The measuring solution 6 which bathes the sensors contains ions at a concentration which gives sufficient conductivity and which does not give rise to greater screening of the active surfaces. It preferably has a neutral pH.

The method for detecting molecular recognitions is based on an approach by comparison, in particular differential comparison. The measurement is carried out using several transistor structures in parallel. The measurement may be differential with respect to the various types of molecules grafted and may optionally include several transistors per type of molecule. It is also possible to compare signals before/after the reaction which reveals the molecular recognition (and/or the evolution during this reaction).

The method according to the invention makes it possible to circumvent the difficulties associated with the sensitivity of an individual sensor to the pH and to the ionic strength and those associated with a variability from one individual transistor to the other (this includes the transistor structure and the quality of the fixing of the probes).

A method according to a preferred embodiment uses the following steps:

a) homogeneous treatments of the entire insulating surface in order to prepare the fixing of the molecular probes;
b) local grafting of various types of molecular probes onto at least some of the individual active surfaces;
c) homogeneous rinsing;
d) electron measurement: the measuring electrolyte is added, the electrode is immersed and the transistors are measured (for example one or more points of the characteristic $I_D$ as a function of $U_{SD}$ and of $U_{SG}$), and the results obtained are compared according to the transistors;
e) homogeneous rinsing;
f) and, optionally, addition of the solution of target molecules in the presence of electrolyte and recognition reaction;
g) homogeneous rinsing;
h) electron measurement, as (d).

In the event that steps f to h are used, it is possible to omit c and d, i.e. to carry out only one electron measurement.

Some transistors which have not been brought into contact with molecular probes (or else a single transistor) can serve as controls. Their characteristics are measured after addition of the measuring electrolyte which, for example, bathes all the transistors.

The grafting of the molecular probes is carried out by depositing microdroplets approximately 100 μm in diameter onto the active surfaces of the transistors using metal micropens which are commercially available.

As shown in FIG. 3, the network of n transistors (for example n=96 transistors) has n drain connections $D_1, D_2 \ldots D_n$ and 2 connections (not represented) equivalent to the common source. The series resistances $R_c$ associated with these connections have values which depend on the index 1 . . . n of the drain.

The values of these resistances $R_c$, produced, for example, by silicon doping, are not negligible.

Figure 4:
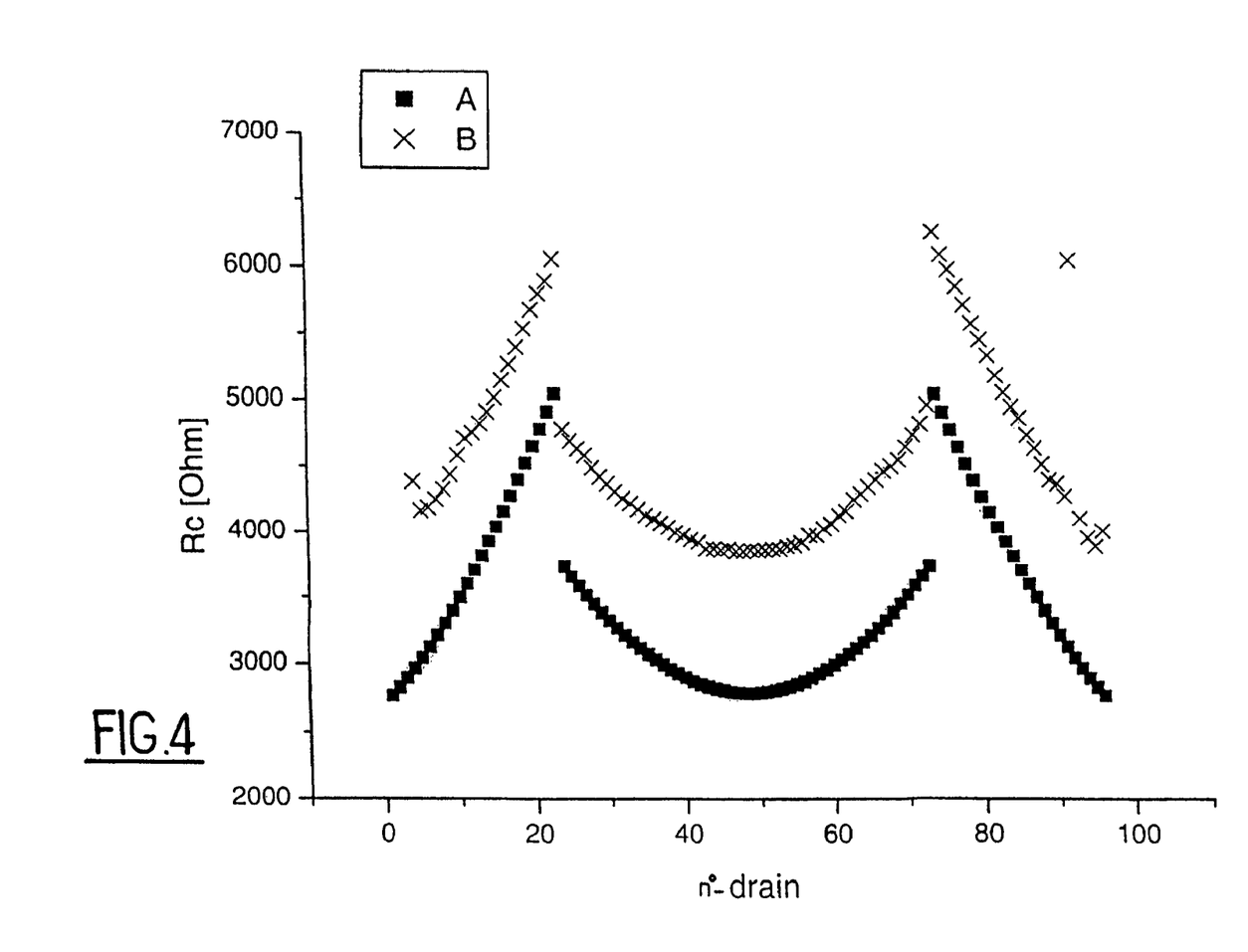

To this effect, the drain connection resistances $R_C$ are calculated from the geometric lengths and cross sections of the doped lines, the resistivity of which is known. The calculation is compared with a measurement of the resistance as a function of the drain index by applying a DC voltage (for example, $U_{SD}$=0.1 V and $U_{SG}$=2 V). This makes it possible to obtain a compensation curve given, by way of example, in FIG. 4.

Figure 5:
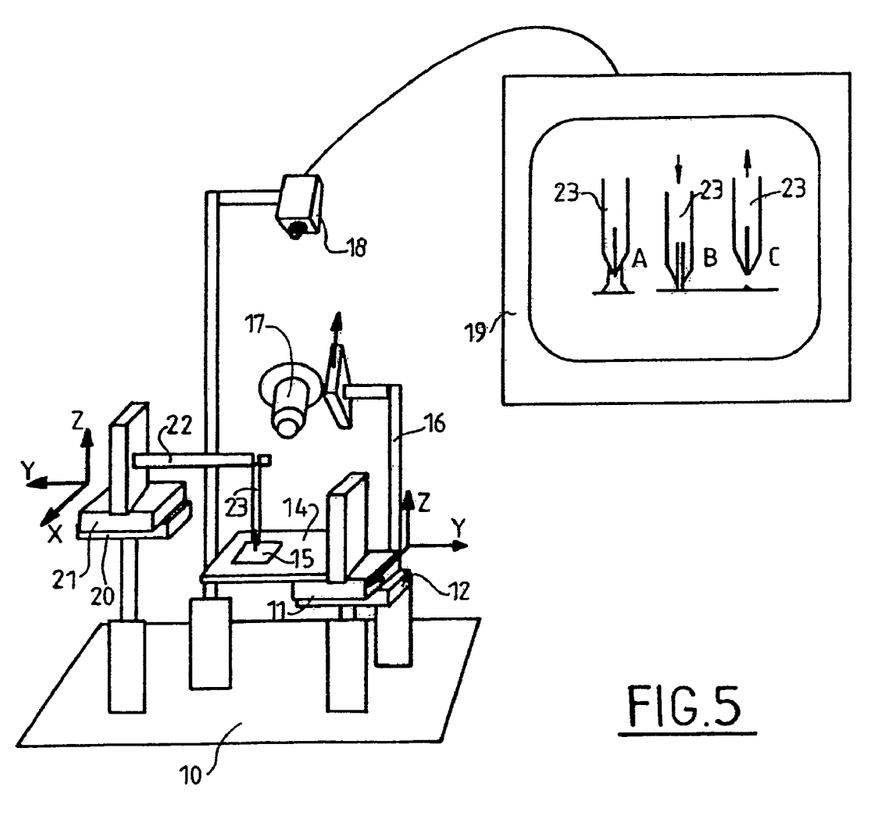
FIG. 5 represents a device for depositing the solution onto selected active zones.

An installation such as that represented in FIG. 5 can be used to implement the method: a platform 12 is placed on a table 10, said platform incorporating a control device comprising a microcontroller for a table 11 providing movement in three perpendicular directions X, Y and Z. A chip 15 incorporating the network of n transistors is placed on a support 14. Another platform 20 comprising a table 21 providing movement in the three directions X, Y and Z is used to move an arm 22 carrying a micro-pen or a pipette 23 for depositing the microdroplets onto at least some of the n transistors. An objective 17 and/or a camera coupled to a screen 19 make it possible to observe the deposition of the microdroplets and to control the operations.

Drain current $I_D$ measurements are carried out with, for example, $U_{SG}$=1 V and $U_{SD}$=0.9 V and a deposited electrolyte of neutral pH which consists of KCl at a content of 0.1 millimol per liter. Since the transistors (p-channel storage transistors) have their sources interconnected, the source voltage or the gate voltage can serve as voltage reference (for example the mass voltage).

An implementation of the method will now be described in connection with FIG. 6.

Before these measurements, an overall treatment of the surface of the Si/SiO$_2$ structure is performed by incubation for 1-2 minutes in sulfochromic acid and rinsing under a stream of deionized water and then incubation for 3 to 5 minutes in a solution of NaOH (60 μl 16N NaOH, 420 μl of ethanol and 220 μl of water) and, finally, rinsing under a stream of deionized water.

Figure 6:
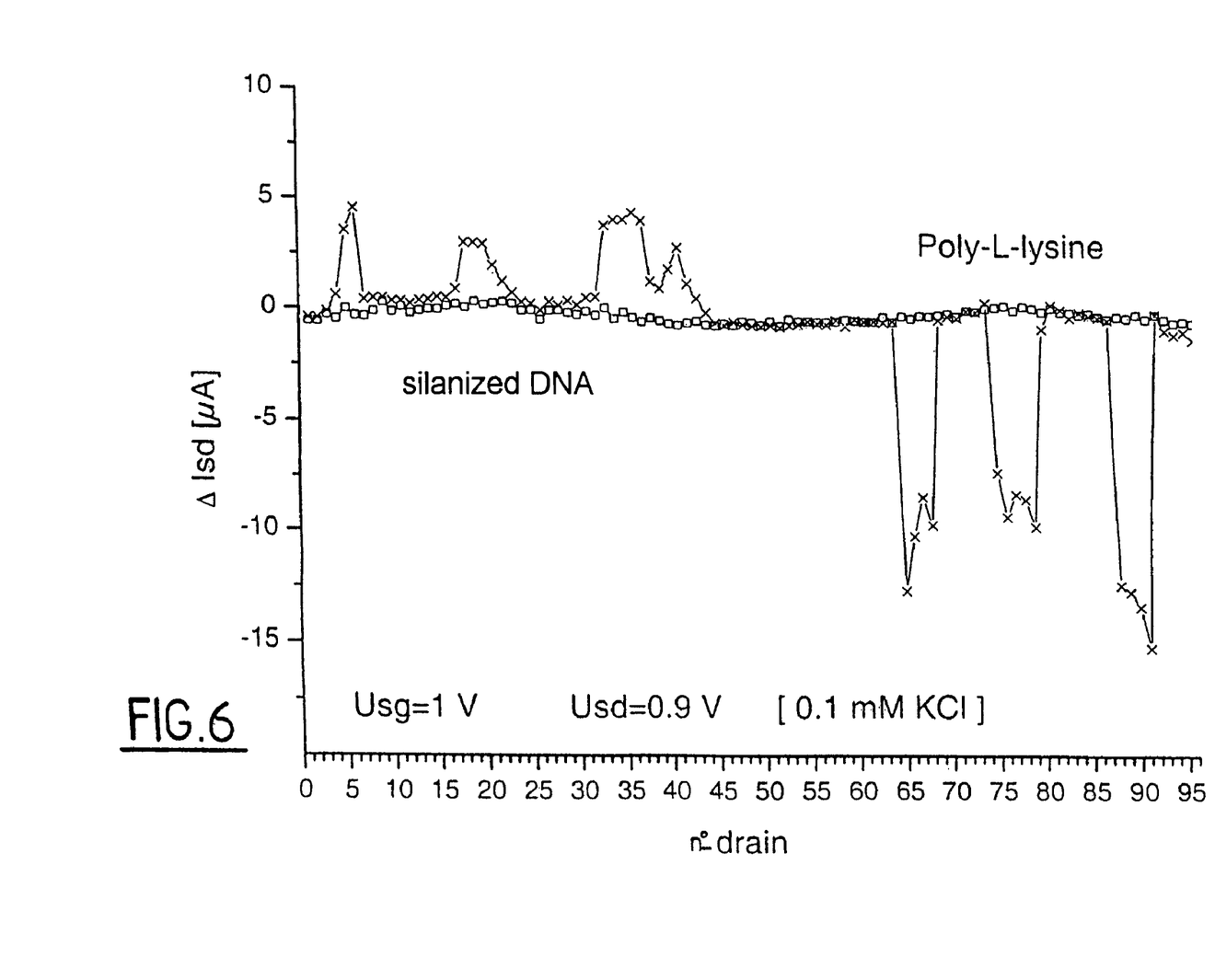
FIG. 6 illustrates the detection of the presence of silanized DNA and of poly-L-lysine with USG and $U_{SD}$ constant, by variation of the drain current $I_{SD}$.

The difference between two measurements carried out before local deposition but before and after rinsing with water is shown as small squares in FIG. 6. The crosses represent the difference between a measurement carried out after local deposition of two different solutions and a measurement carried out before deposition (the measurement carried out before the rinsing with water).

Using a commercial pin 23 (Telechem SMP3B) mounted on the device 22 shown in FIG. 5, a solution 1 is deposited onto the transistors 5-7 (with contact between pin and surface), the transistors 19-21 and the transistors 33-37, and a solution 2 deposited onto the transistors 66-69, the transistors 76-79 and the transistors 87-89.

Solution 1: 0.5 μl of 20 mer oligonucleotide thiol-modified in the 5' position at 1 nmol/μl, 9 μl 30 mM sodium acetate pH 4.3, 0.5 μl 5 mM mercaptosilane in sodium acetate, which is left to react for one hour at ambient temperature before deposition.

Solution 2: Poly-L-lysine (0.01% weight/volume "w/v" final concentration (P8920, Sigma)) in a 0.1×PBS buffer at pH 7.

After the local depositions, the sample is dried for 15 minutes in a humid atmosphere and then for 5 minutes at 50° C.

The poly-L-lysine is positive in the measuring electrolyte (neutral pH) due to the ionized amine groups. The decrease in current observed on the poly-L-lysine deposits is compatible with the adsorption of a positive charge onto the surface.

For solution 1, the silane modification on the DNA reacts with the OH groups of SiO$_2$ and the DNA is negatively charged in solution.

Solutions 1 and 2 therefore give signals of opposite signs.

Figure 7:
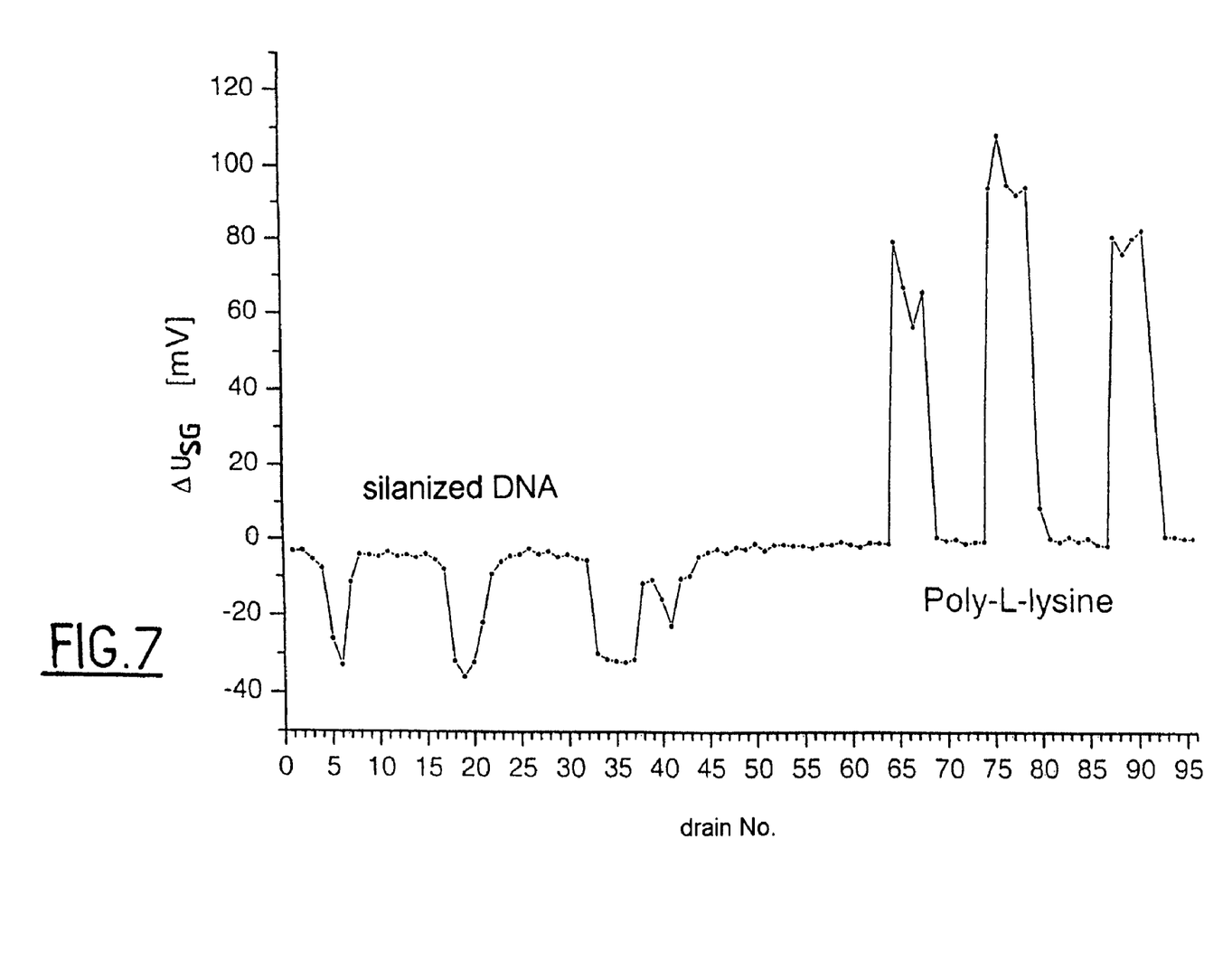
FIG. 7 illustrates the detection of the presence of silanized DNA and of poly-L-lysine with $I_{SD}$ and $U_{SD}$ constant, by detection of the variation in voltage USG.

Another implementation of the method will now be described in connection with FIG. 7.

The difference in surface potential $\Delta U_{SG}$ corresponding to the measurement before/after deposition is measured. In order to determine $\Delta U_{SG}$, the two-dimensional characteristic, for example $I_D(U_{SG}, U_{SD})$, is measured and the intrinsic characteristics of the 96 transistors are determined by correcting numerically as a function of the resistances $R_C$ of the drain lines in series. The modification of the condition of the SiO$_2$ interface induces a change in the intrinsic characteristics which corresponds to a shift $\Delta U_{SG}$ at constant $U_{SD}$ and drain current $I_D$. This shift makes it possible to directly obtain an independent measurement of the operating point of the transistor, unlike the change in current $\Delta I_D$ presented in FIG. 6. The value $\Delta U_{SG}$ makes it possible, in first approximation, to quantify the change in the SiO$_2$/liquid interface induced by the local deposit. According to a variant, $U_{SG}$ is varied so as to keep $I_D$ constant.

Figure 8A:
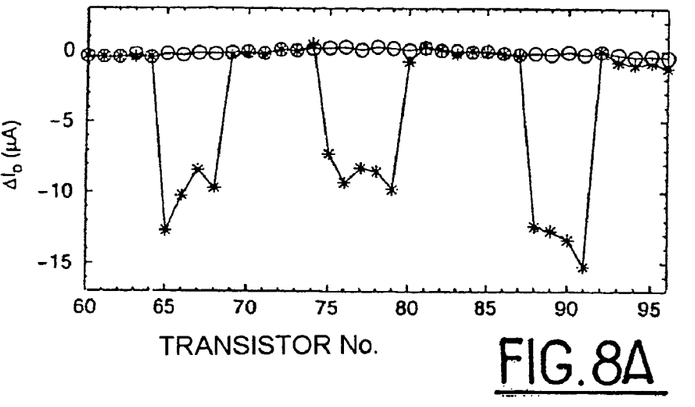
FIGS. 8A to 8C represent the results of experiments carried out under various experimental conditions.
Figure 8B:
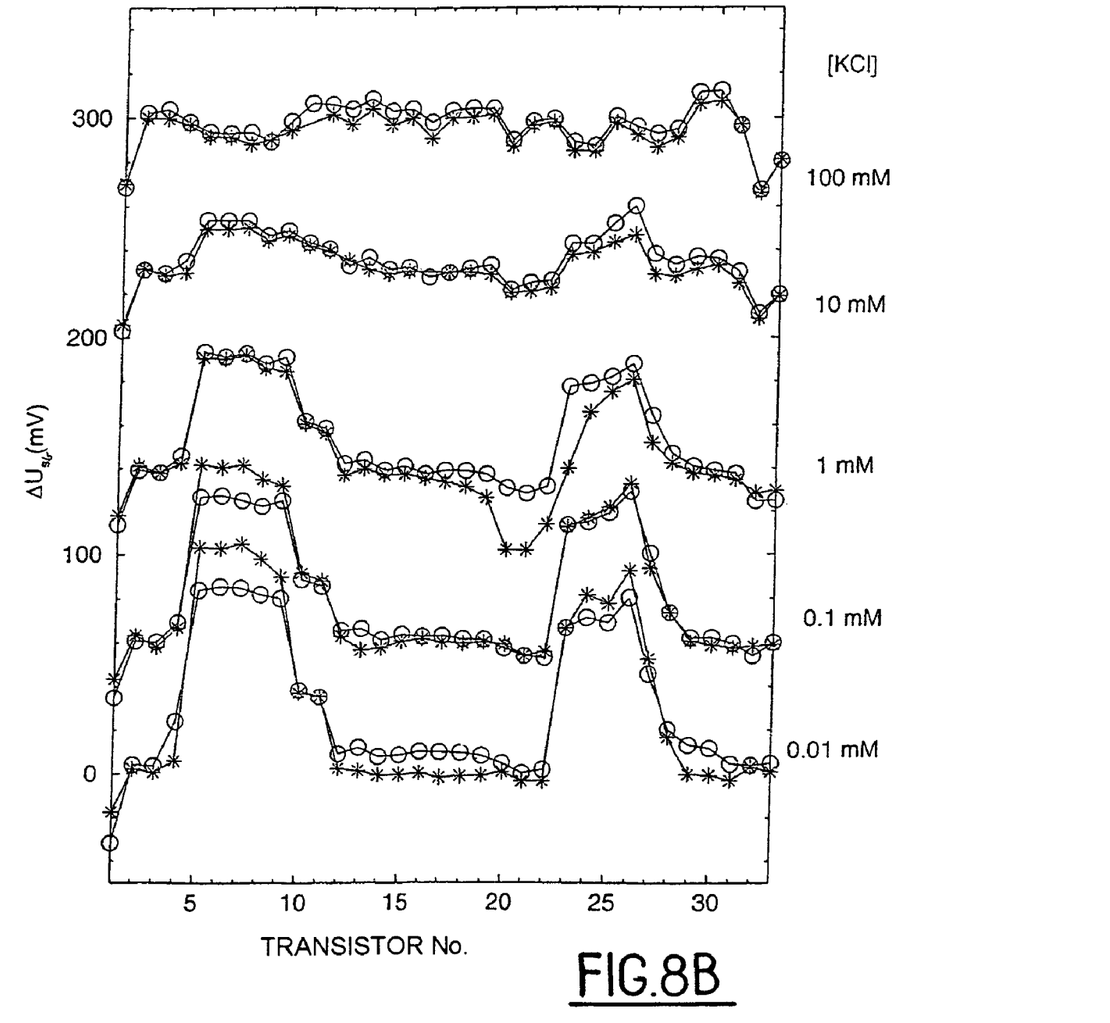
Figure 8C:
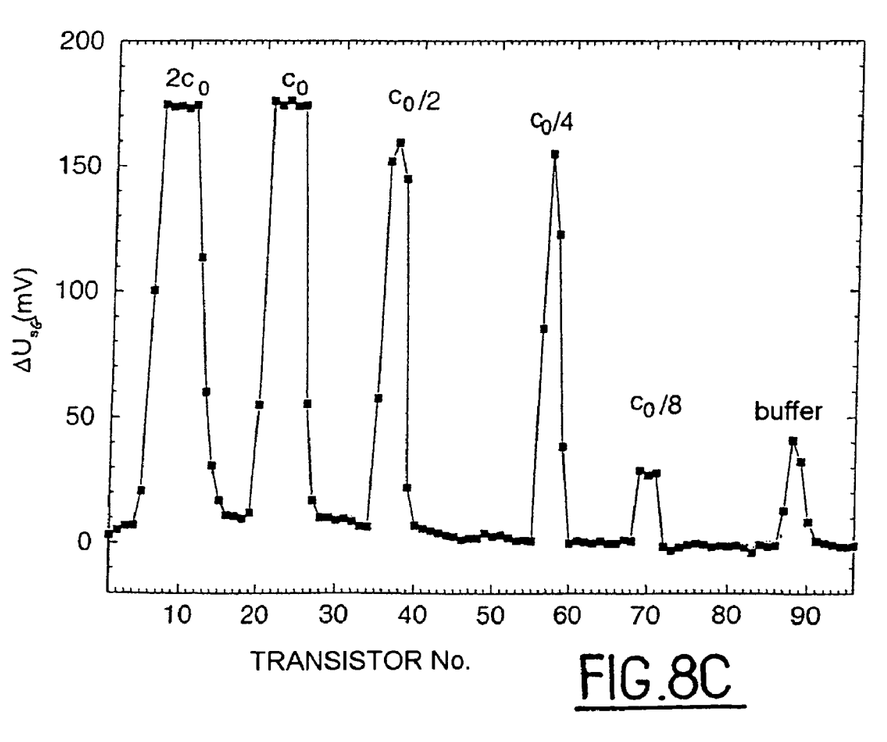

FIGS. 8A to 8C show differential measurements carried out before and after deposition of poly-L-lysine (FIG. 8A), carried out as a function of the concentration of KCl (FIG. 8B), and carried out as a function of the concentration of deposited poly-L-lysine.

In FIG. 8A, the variations $\Delta I_D$ in the drain current $I_D$ are represented on the Y-axis for each of the transistors 60 to 96 identified on the X-axis ($U_{SG}$=1 V, $U_{SD}$=0.9 V and electrolyte KCl at 0.1 mM). The differences $\Delta I_D$ between two measurements carried out before a local deposition but separated by rinsing with water are represented by circles. The differences $\Delta I_D$ corresponding to measurements carried out before and after a local deposition of poly-L-lysine are represented by stars. After the local deposition, the sample is left at ambient temperature for 15 minutes in humid medium, before being dried at 50° C. for 5 minutes. The dilution $C_o$ of the poly-L-lysine is 0.01% weight/volume "W/V" final concentration (P8920, Sigma) in a 0.1×PBS buffer at pH 7.

In FIG. 8B, the differences $\Delta U_{SG}$ in the source-gate voltage $U_{SG}$ are measured on some of the transistors of a network of 62 FET transistors with $U_{SD}$=1.2 V and $I_D$=50 μA. The differences between a reference measurement (carried out before local deposition and with a concentration of KCl of 0.01 mM) and two series of measurements (carried out after local deposition of poly-L-lysine and with various concentrations of KCl) are represented by circles and stars. Here, a local deposition of poly-L-lysine was carried out in two distinct zones with the same dilution $C_o$ as in the case of FIG. 8A. In each of the two series of measurement, the concentration of KCl in the measuring buffer is varied between 0.01 mM and 100 mM, the range including the values 0.1 mM, 1 mM and 10 mM. The surface is rinsed with water between the two series of measurement. A notable sensitivity of the detection of poly-L-lysine is observed for KCl concentrations of between 0.01 mM and 1 mM, and the height of the peaks gradually decreases beyond these values.

FIG. 8C shows the variations $\Delta U_{SG}$ in the voltage $U_{SG}$ as a function of the concentration of polymer deposited (poly-L-lysine), i.e. $2C_o, C_o, C_o/2, C_o/4, C_o/8$, in a 0.1×PBS buffer, pH 7, $C_o$ having the value indicated for the measurements in FIG. 8A. The measuring conditions are as follows: $U_{SD}$=1 V, $I_D$=100 µA, and a concentration of 0.01 mM for KCl. These measurements show that there is no advantage, under the experimental conditions chosen, in increasing the concentration beyond $C_o$.

FIGS. 9A to 9D show the electronic detection of DNA. The voltages $U_{SG}$ and the variations $\Delta U_{SG}$ in the voltage $U_{SG}$ correspond to an operating point $U_{SD}$=1 V, $I_D$=100 µA and a KCl concentration of 0.01 mM. They are obtained from the characteristic $I_D$ ($U_{SG}$, $U_{SD}$) and are recorded on the curves with the FET transistor number (1 to 96) on the X-axis.

The stars represent the measurement before initial surface treatment with sodium hydroxide as indicated above in connection with FIG. 6. The circles represent the measurement after incubation of poly-L-lysine on the entire network. In order to allow immobilization of DNA, the network of FET transistors is incubated for 30 minutes in a dilution of poly-L-lysine (concentration Co). Next, without any prior drying, rinsing is carried out with water, followed by air-drying. The incubation results in shifts in the voltage $U_{SG}$ by a value of 97±50 mV (statistical value over 67 surfaces prepared), which reduce the variations between transistors in the electronic signal. The shifts are compatible with those observed with the values measured in relation to FIG. 8C on local deposits at the same concentration. The squares represent the measurements after local deposition of oligonucleotides (5' Cy-5 modified 20 mer oligonucleotides, concentration 50 µM in deionized water) around transistor Nos. 30, 60 and 90. The image in microfluorescence of the abovementioned three DNA points is represented in level of gray and above FIG. 9A.

Figure 9A:
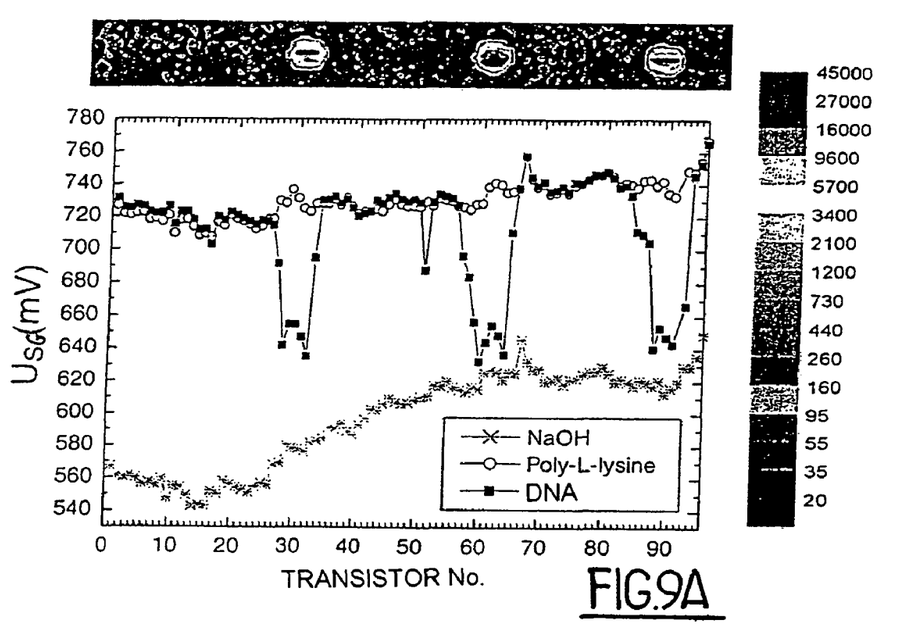
FIGS. 9A to 9D show electronic detection of DNA.
Figure 9B:
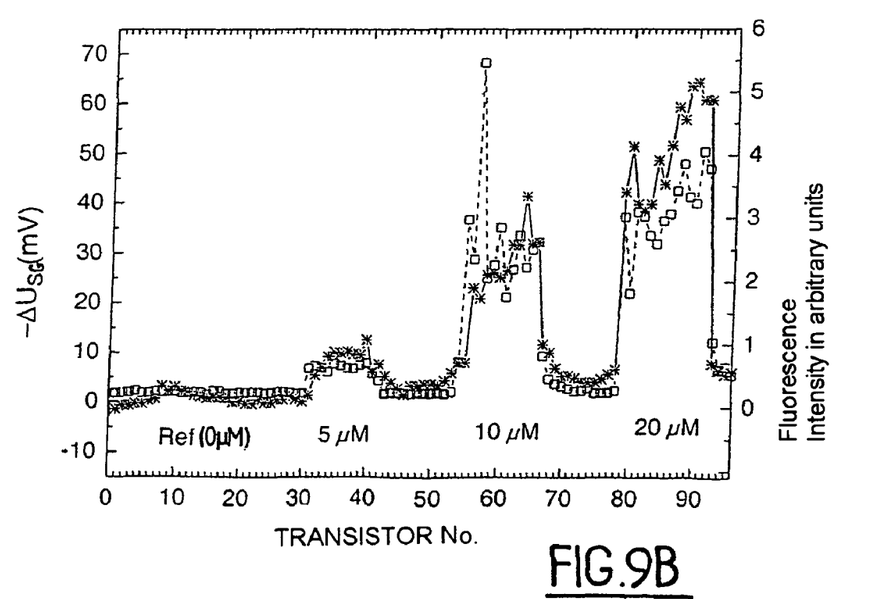

FIG. 9B shows the electronic detection and detection by fluorescence of Cy5 modified oligonucleotides. The points represented by stars were obtained by the difference $\Delta U_{SG}$ between two electron measurements carried out before and after four local depositions with different concentrations of DNA (Ref.=0 µM, 5 µM, 10 µM, 20 µM). They show the variation $\Delta U_{SG}$ in the voltage $U_{SG}$ which is observed in the characteristics of the transistors and which is due to the local deposits of DNA. The squares show the intensity of the fluorescence measured on the dried FET transistors, once the electron measurement has been carried out with the electrolyte. It will be noted that the same electronic detection is obtained with oligonucleotides of the same type but which are not modified.

Figure 9C:
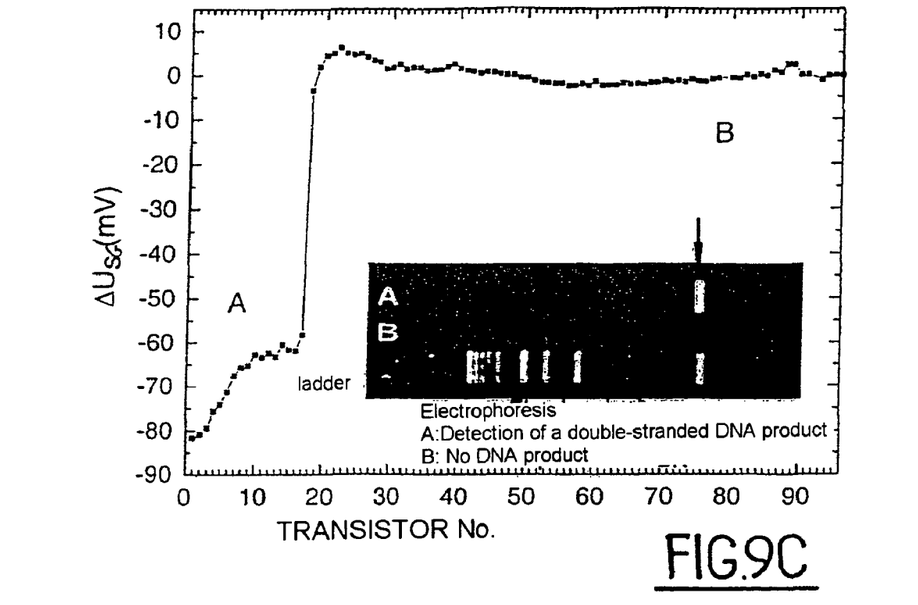

FIG. 9C shows the detection of double-stranded DNA after macroscopic deposition of two products onto two zones A and B of the FET transistors. 0.15 µl taken from two tubes A and B is deposited, using a micropipette, onto two respective regions of the network of FET field-effect transistors. The network was precovered with poly-L-lysine in order to immobilize the DNA, and measured so as to serve as a reference. Zone A (transistors 1 to 20) in FIG. 9C was covered with a solution from tube A and zone B (transistors 50 to 90) with the solution from tube B, allowing a non-covered central region (transistors 21 to 49) to remain between them. Incubation is carried out for 15 minutes without drying, followed by rinsing with water, and the transistors of the network are then measured. Transistors 1 to 20 (zone A) were incubated with a solution containing products of a polymerase chain reaction (PCR) obtained in tube A according to the procedure described below. A downward shift is noted in this zone compared with zone B (transistors 50 to 90) and compared with said nonincubated zone between A and B. In fact, the reference solution used in zone B was chosen so as not to produce double-stranded DNA (tube B according to the procedure described below).

Figure 9D:
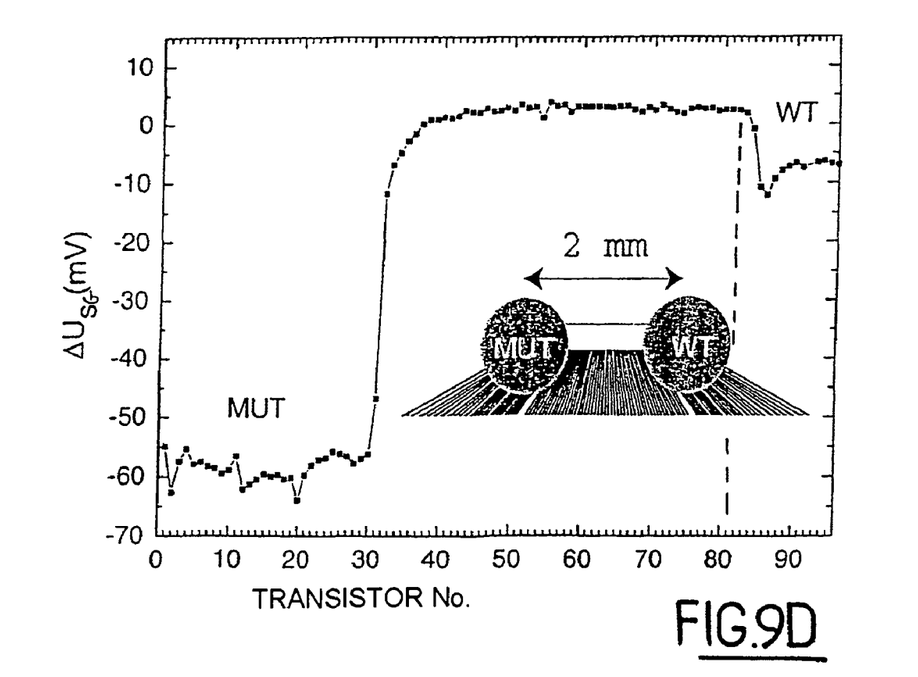

In FIG. 9D, in the MUT region (transistors 1 to 35) onto which has been deposited a solution obtained by PCR amplification under conditions described below, from DNA carrying a mutation, a downward shift of $\Delta U_{SG}$ is observed, whereas, in the reference region WT for which the starting DNA does not carry the mutation, no such shift is observed.

For the experiment in FIG. 9C, the technique for PCR amplification of a 1009 base pair DNA fragment uses bacteriophage λ DNA digested with the BstEII enzyme, using two primers:

5' - CCG CGA ACT GAC TCT CCG CC (SEQ ID NO: 1)

3' - CAG GCG GCA GGG CTG ACG TT (SEQ ID NO: 2).

The PCR protocol is carried out on a commercial thermocycler:
initiation for 3 minutes at 94° C.,
30 cycles of denaturation/hybridization/extension for 30 seconds at 94° C./30 seconds at 57° C./and 2 minutes at 72° C.

A final PCR step is carried out for 3 minutes at 72° C.

For a volume of 50 microliters, 10 nanograms of λ DNA digested with BstEII are used, 20 picomol for each of the primers, and the four dNTPs each have a final concentration of 50 µM. 0.5 microliters of TAQ polymerase (at 1 U/µl) from Roche Diagnostics is placed in the standard PCR reaction buffer (supplied with the TAQ polymerase). This corresponds to the preparation from tube A for zone A. In the reference tube B (which corresponds to zone B), one of the four dNTPs, namely the dTTP, is replaced with dCTP, in such a way as to conserve the same total concentration of dNTPs, which inhibits the synthesis of the double-stranded DNA product.

The PCR products are, in both cases, purified twice on "QIAQUICK" columns from the company Qiagen and eluted with a Tris-Cl buffer, pH 8.5, at a concentration of 10 mM.

The specific PCR amplication of the mutation used in the context of the experiment corresponding to FIG. 9D is based on a fragment of the human CX-26 gene (accession code M 86849, chromosome 13q11-12). This gene is amplified from genomic DNA originating from one or more patients. The PCR technique uses cycling primers and conditions described in the articles by F. DENOYELLE et al., used for the first "Prelingual Deafness: high prevalence of a 30delG mutation in the connexin 26 gene" published in Human Molecular Genetics, 1997, Vol. 6, No. 12, p. 2173-2177 and for the second "Clinical features of the prevalent form of childhood deafness, DFNB1, due to a connexin-26 gene defect: implications for genetic counselling" published in the THE LANCET, Vol. 353, Apr. 17, 1999, p. 1298 to 1303. A Pwo polymerase (from Roche Diagnostics) is used in a PCR buffer with MgSO$_4$ at 1.5 mM. The primers are GAP1F and CONNR (see the second abovementioned article by F. DENOYELLE, p. 1299, right-hand column, penultimate paragraph) and the experimental conditions are those of the abovementioned first article by the same author (p. 2177). A final concentration of 0.6 µM is used for each of the primers and of 0.2 mM for each of the dNTPs.

The PCR products are purified on "QIAQUICK" columns from the company Qiagen and, after a dilution (10 000-fold) serve as starting DNA in the reaction specific for the mutation, which subsequently takes place.

The PCR amplification is chosen so as to allow detection of the mutation 35delG (or 30delG) in the CX26 gene by means of primers specific for this mutation. The cycling conditions and the sequences of the primers are given in the article by G. LUCOTTE et al., entitled "PCR test for diagnosis of the common GJB2 (connexin 26) 35delG mutation on dried blood spots and determination of the carrier frequency in France" published in Molecular and Cellular Probes (2001) 15 p. 57 to 59. 20 picomol of each of the primer oligonucleotides are used for a final volume of 50 μl.

The two primers specific for the mutation (see abovementioned article by LUCOTTE, page 58, right-hand column, M primer and N primer) and a common primer (C primer) are used to synthesize the 197 base pair PCR products. Two specific PCR reactions are carried out on each DNA sample, the first of these reactions is carried out with the first specific primer and gives a product if the mutation is present in the starting DNA. The second reaction is carried out with the second specific primer and gives a product if the mutation is not present in the starting DNA. This makes it possible to determine whether a sample is normal, heterozygous or homozygous with respect to this mutation.

Figure 10A:
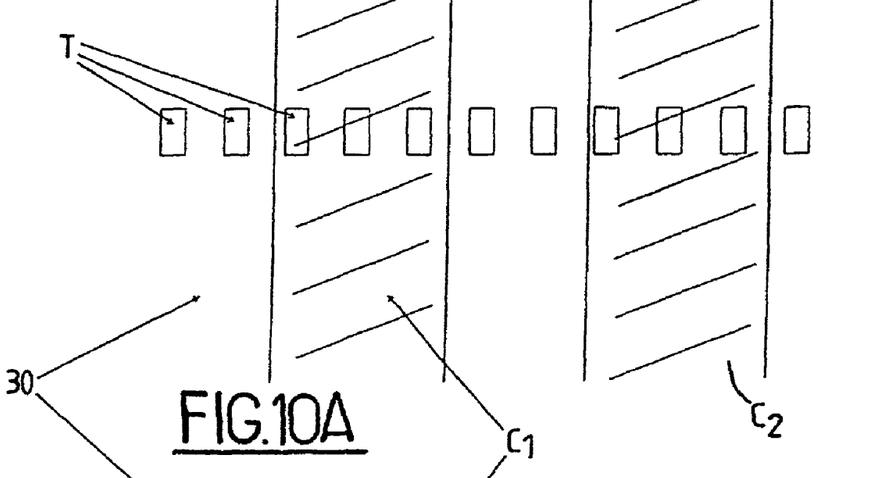
FIGS. 10A and 10B illustrate the use of microfluid channels.
Figure 10B:
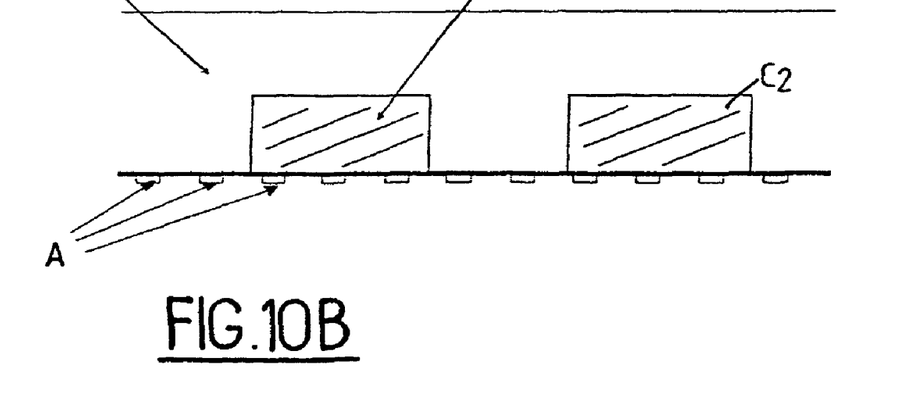

It is thus possible to carry out differential measurements using two solutions which circulate in the two channels $C_1$ and/or $C_2$. It is also possible to produce a large number of such microfluid channels on the same substrate 30, the substrate in which they are arranged being attached to the semiconductor substrate in which the FET field-effect transistors are integrated. It is also possible to measure a variation within a given channel. This variation may be over time. It is also possible to inject various solutions at a given place in the capillary, and the profile of the concentrations remains unchanged along the channel even at a great distance from the injection point. Reference will be made to the article by Paul J. A. KENIS et al., entitled "Microfabrication inside Capillaries Using Multiphase Laminar Flow Patterning", published in SCIENCE, vol. 285, Jul. 2, 1999, p. 83-85 (in particular FIG. 1A).

An analytical technique using microfluidics is described in the article "Monolithic integrated microfluidic DNA amplification and capillary electrophoresis analysis system" by Eric T. LAGALLY et al., published in Sensors and Actuators B 63 (2000), p. 138-146.

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA

<400> SEQUENCE: 1
ccgcgaactg actctccgcc                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA

<400> SEQUENCE: 2
caggcggcag ggctgacgtt                                          20
```

For a volume of 50 μl of reactive medium, in a standard PCR buffer, one microliter of DNA originating from the preamplification described above, 30 picomol of each of the primers, dNTPs at a content of 100 μM and 1 microliter of TAQ polymerase (1 U/μl) from Roche Diagnostics are used. The PCR products are purified twice on "QIAQUICK" columns from the company QIAGEN, and eluted with a Tris-Cl buffer at 10 mM, pH 8.5. The same pair of primers: C-primer and M-primer, are used for the WT and MUT tubes. The only difference is the starting DNA.

FIGS. 10A and 10B show an integrated circuit having transistors T arranged along a line (or several lines). Two microfluid channels (for example parallel channels) $C_1$ and $C_2$ of a substrate 30 make it possible to bring one or more field-effect transistors T into contact with the solution which circulates in a channel $C_1$ and/or $C_2$. The material of a substrate 30 which comprises the microfluid channels (or capillaries) may be a PDMS (polydimethylsiloxane) or other polymer, a glass, silicon, etc.

The invention claimed is:

1. A method for detecting at least one parameter representative of molecular probes fixed to active zones of a sensor, wherein said sensor includes a network of field-effect transistors, each of which has a source region, a drain region, and a gate region which forms one of said active zones on which said representative parameter is detected, the method comprising the following steps:
    a) bringing some of said active zones into contact with molecular probes in order to fix said probes;
    b) bathing at least some of said active zones which have been brought into contact with said molecular probes, in an electrolyte solution;
    c) measuring at least one point of at least one of a drain current, source-gate voltage, and source-drain voltage characteristic of at least two of the field-effect transistors having at least two active zones that are part of said some of active zones, corresponding to a first group, so as to deduce therefrom said representative parameter by comparison between at least two measurements obtained for two different active zones immerged in said electrolyte solution; and fixing a potential of the electrolyte solution which covers said active zones with an electrode that applies a gate source voltage to the field effect transistors, the electrode being immerged in said electrolyte solution.

2. The method as claimed in claim 1, wherein said measuring of said at least one point comprises:

applying a given voltage between the drain region and the source region of at least said transistors of the first group and also the application, in a first case, of a given voltage between the gate region and the source region of these transistors of the first group or, in a second case, of a given drain current to the transistors of the first group.

3. The method as claimed in either of the preceding claims, further comprising: a rinsing step between a) and b).

4. The method as claimed in claim 1, further comprising, after a) and before b), the following steps:
a1) rinsing,
a2) adding a solution containing target molecules capable of interacting specifically with the molecular probes.

5. The method as claimed in claim 1, further comprising, after step c), the following steps:
d) adding an electrolyte solution containing target molecules capable of interacting specifically with the molecular probes;
e) measuring at least one point of a drain current, source-gate voltage, and source-drain voltage characteristic of at least two transistors of a second group corresponding to said active zones brought into contact with said molecular probes and with said target molecules, so as to obtain by comparison at least one said representative parameter.

6. The method as claimed in claim 5, wherein, in step e), the measurement of at least one point of the characteristic comprises:

applying a given voltage between the drain region and the source region of said two transistors of the second group, and applying, in a first case, a given voltage between the gate region and the source region of the transistors of the second group or, in a second case, of a given drain current to the transistors of the second group.

7. The method as claimed in claim 5, comprising: using a plurality of said measurements of at least one point of the characteristic, which are spaced out over time.

8. The method as claimed in claim 1, wherein said comparison is carried out by differential measurement.

9. The method as claimed in claim 1, wherein the comparison is carried out between measurements carried out on at least two transistors corresponding to said active zones which are bathed in said electrolyte solution after having been brought into contact with said molecular probes.

10. The method as claimed in claim 1, wherein the comparison is carried out between measurements carried out on at least one transistor corresponding to a first active zone which is bathed in said electrolyte solution after having been brought into contact with said molecular probes for the purpose of fixing the molecular probes, and on at least one transistor corresponding to a second active zone which is bathed in said electrolyte solution without having been brought into contact with said molecular probes.

11. The method as claimed in claim 1, wherein said representative parameter is a detection of the fixing of the molecular probes to said one of said active zones.

12. The method as claimed in claim 1, wherein the molecular probes are DNA, RNA or protein molecules.

13. The method as claimed in claim 12, wherein the molecular probes are DNA molecules and the field-effect transistors are of depleted n-channel type, with a negative gate bias.

14. The method as claimed in claim 12, comprising:
using detection by comparison between two zones, each zone comprising at least one field-effect transistor, the first zone being bathed in a solution obtained from a first enzymological reaction in the first zone giving a detectable product specific for the presence or the absence of a mutation in a first DNA sample, and the second zone being bathed in a solution obtained from a second enzymological reaction in the second zone giving a DNA product specific for the presence or for the absence of a mutation in a second DNA sample.

15. The method as claimed in claim 14, wherein the first and the second DNA samples originate from two patients and the first and second enzymological reactions are the same for the two samples.

16. The method as claimed in claim 14, wherein the first and the second DNA samples are identical and originate from the same patient, and the first enzymological reaction in the first zone is carried out under experimental conditions producing a DNA product in the absence of mutation in the first sample, and the second enzymological reaction in the second zone is carried out under experimental conditions producing a DNA product in the presence of a mutation in the second sample.

17. The method as claimed in claim 1, comprising: circulating a solution through at least one microfluid channel, so as to bring said solution into contact with at least one field-effect transistor.

18. The method as claimed in claim 1, wherein the electrode is Ag/AgCl.

* * * * *